United States Patent [19]

Leonard

[11] 4,344,746
[45] Aug. 17, 1982

[54] DISTRIBUTOR FOR THE PROGRESSIVE AND REVERSIBLE SUPPLY OF AN AIR MOTOR, IN PARTICULAR FOR HAND-HELD DENTAL INSTRUMENTS

[75] Inventor: Henri Leonard, Besancon, France

[73] Assignee: Societe Micro-Mega S.A., Besancon, France

[21] Appl. No.: 141,645

[22] Filed: Apr. 18, 1980

[30] Foreign Application Priority Data

Apr. 20, 1979 [FR] France .................................. 79 10720

[51] Int. Cl.³ ........................ F01C 13/02; F01C 21/14
[52] U.S. Cl. ..................................... 418/270; 415/503
[58] Field of Search ........................... 418/270; 415/503

[56] References Cited

U.S. PATENT DOCUMENTS

| | | | |
|---|---|---|---|
| 3,429,230 | 2/1969 | Quackenbush | 418/270 |
| 3,439,422 | 4/1969 | Doeden et al. | 418/270 |
| 3,942,392 | 3/1976 | Page, Jr. et al. | 415/503 |
| 4,040,311 | 8/1977 | Page, Jr. et al. | 415/503 |
| 4,120,623 | 10/1978 | Lohn | 418/270 |
| 4,167,062 | 9/1979 | Page, Jr. et al. | 415/503 |

Primary Examiner—John J. Vrablik
Attorney, Agent, or Firm—Nathaniel A. Humphries

[57] ABSTRACT

An air distributor for the supply of a blade-type motor which can be rotated about its axis by means of a sleeve with which it is integral external to a casing, the rear end plate of the blade-type motor being constituted by a ring traversed by at least three openings which are off set at angles of 120°, characterized in that the end of the distributor facing the said ring is shaped so as to form, on the one hand, a chamber causing the outlet openings of the motor block to communicate with one or more outlet pipes for the air toward the exterior traversing the distributor and, on the other hand, a surface in direct contact with the said ring, on which surface there merges a feed duct for air traversing the said distributor originating from the compressed air source.

Application: to hand-held dental instruments.

8 Claims, 4 Drawing Figures

DISTRIBUTOR FOR THE PROGRESSIVE AND REVERSIBLE SUPPLY OF AN AIR MOTOR, IN PARTICULAR FOR HAND-HELD DENTAL INSTRUMENTS

The present invention relates to a compressed air distributor for a blade-type motor, in particular for driving hand-held dental instruments, which allows the rotational speed of the blade-type motor to be controlled and reversed.

Blade-type motors have been known for a long time and have many uses, in particular as motors for driving hand-held dental instruments, on which the said dental instruments can be fixed, for example, by the fastening device forming the subject of French Pat. No. 1,483,766.

All these motors are based on the same principle of a rotor turning in an eccentric hollow cylindrical stator, the said rotor being provided with blades which slide in radial slots and divide the space between the rotor and the stator into several chambers. At least one compressed air inlet opening and at least one air outlet opening are provided, both merging into the space between the rotor and the cylindrical internal wall of the stator. The compressed air arriving through the air inlet opening (or one of the openings) expands in one of the chambers, pushing the corresponding blade and thus rotating the integral rotor, and escapes from the motor through the outlet opening or openings. Rotational speeds of the order of 20,000 rpm can be achieved with this type of motor. A motor of this type is described, for example, in German Patent Application No. 2,304,666.

Devices for reversing the direction of circulation of the compressed air so as to reverse the direction of rotation of the motor have already been proposed as well. This is particularly useful for dentists. This is the case, for example, in French Pat. Nos. 1,486,311 and 2,016,575, in which the reversal is effected by a slide valve. With this type of device, the roles of the inlet and outlet ducts actually have to be reversed by branching the feed tube for air originating from the compressed air source in a different manner. This device is impractical because it has to be handled many times and this is unacceptable for dental use.

Air distributing devices for the supply of a blade-type motor are therefore needed, in particular for hand-held dental instruments, which are simple to use and which allow the rotational speed of the motor to be regulated and reversed by manual operations which are easy for the user.

According to the invention, this result is achieved by proposing an air distributor for the supply of a blade-type motor, the air distributor and the blade-type motor each being arranged inside the same casing, the said distributor being rotatable about its axis by means of a sleeve with which it is integral and which is external to the casing, the rear end plate of the blade-type motor being constituted by a ring perforated by at least three openings offset at angles of 120°, one of the openings still being an outlet opening, the two other openings of equal diameter being the inlet opening and the outlet opening respectively, depending on the rotational direction selected for the motor, characterized in that the end of the distributor facing the said ring is shaped so as to form, on the one hand, a chamber causing the outlet openings of the motor block to communicate with one or more outlet pipes for the air toward the exterior, traversing the distributor and, on the other hand, a surface in direct contact with the said ring, on which surface there merges a feed duct for air traversing the said distributor and originating from the source of compressed air, the said feed duct being able to communicate progressively with the compressed air inlet orifice of the said ring by rotation of the distributor about its axis, in such a manner that the feed duct for air traversing the distributor never communicates with the chamber causing the motor block outlets to communicate with the outlet pipes for the air traversing the distributor.

According to a preferred embodiment of the invention, the progressive communication of the air intake duct with that of the inlet openings in the ring corresponding to the desired rotational direction of the motor will be effected by providing round the delivery orifice of the air intake duct at the end of the distributor facing the ring, an annular end seal joint of rectangular cross-section and of a width which is at least equal to the diameter of the inlet opening of the ring. According to another preferred embodiment of the invention, the surface of the distributor will comprise a shoulder in which the annular end seal joint will be arranged surrounding the delivery orifice of the air feed duct, while the chamber causing the motor block outlets to communicate with the outlet pipes for the air traversing the distributor have a complementary crescent shape.

This annular seal joint does in fact have two functions, that is to say, on the one hand, it ensures the seal at the level of the seal joint between the distributor and the various openings in the ring on the one hand, and, on the other hand, allows regulation and reversal of the rotational speed of the motor on the other hand.

To ensure an optimum seal at this level, which guarantees the maximum utilisation of the power supplied by the compressed air, it must be possible to slap the annular end seal joint against the end facing the ring without preventing the rotation of the distributor supporting the said seal joint.

This result is achieved according to another characteristic of the invention by recognising that it is the pressure of the compressed air supply which will slap the seal joint against the ring with the aid of suitable means arranged along the air supply passage. These means can consist, for example, of a flat annular surface subjected directly to the pressure of the air supply, the said surface being arranged at the rear end of the distributor substantially perpendicularly to the axis of the said distributor. As a result, it should also be recognised with this embodiment that the distributor should be free to shift axially to allow the annular end seal joint to be placed under pressure and to return to its rest position when it is not operating. An annular compensating chamber preferably communicating with the atmosphere will be provided for this purpose to prevent the creation of a vacuum which would oppose the force of pressure of the compressed air on the annular seal joint.

It is also proposed, to ensure the supply of compressed air to the distributor whatever its position, that the rear portion of the distributor co-operate with a casing comprising an annular chamber in which merges the intake of air originating from the source, the annular chamber communicating permanently with the intake pipe for air traversing the distributor.

Rotation is effected from the exterior by means of a sleeve which is made integral with the said distributor, for example by a screw also traversing the casing in which the distributor is arranged, the rotation of the said sleeve preferably being limited to a total of 120°, the screw making the sleeve integral with the distributor also acting as an abutment for this purpose. The two terminal positions for the movement of the sleeve correspond to the maximum rotational speeds of the motor in each direction, the intermediate position corresponding to a zero speed of the motor when neither of the supply orifices is supplied, that is to say in communication with the feed duct for air traversing the distributor. Corresponding markings can be engraved on the exterior of the sleeve.

Finally, various sealing O-rings will be provided on the distributor as they are needed, in addition to the annular end seal joint, to ensure the respective seal between:

(a) the distributor and the casing in which it is arranged;

(b) the chamber for compensating the expansion of the joint which is exposed to the atmosphere and the air intake;

(c) the intake of air into the distributor, in particular the annular chamber ensuring a constant supply on the one hand and the pipes for the outlet of air through the same distributor.

The invention will be understood better with the aid of the following description of a preferred embodiment of the invention and the attached drawings.

Figure 1:
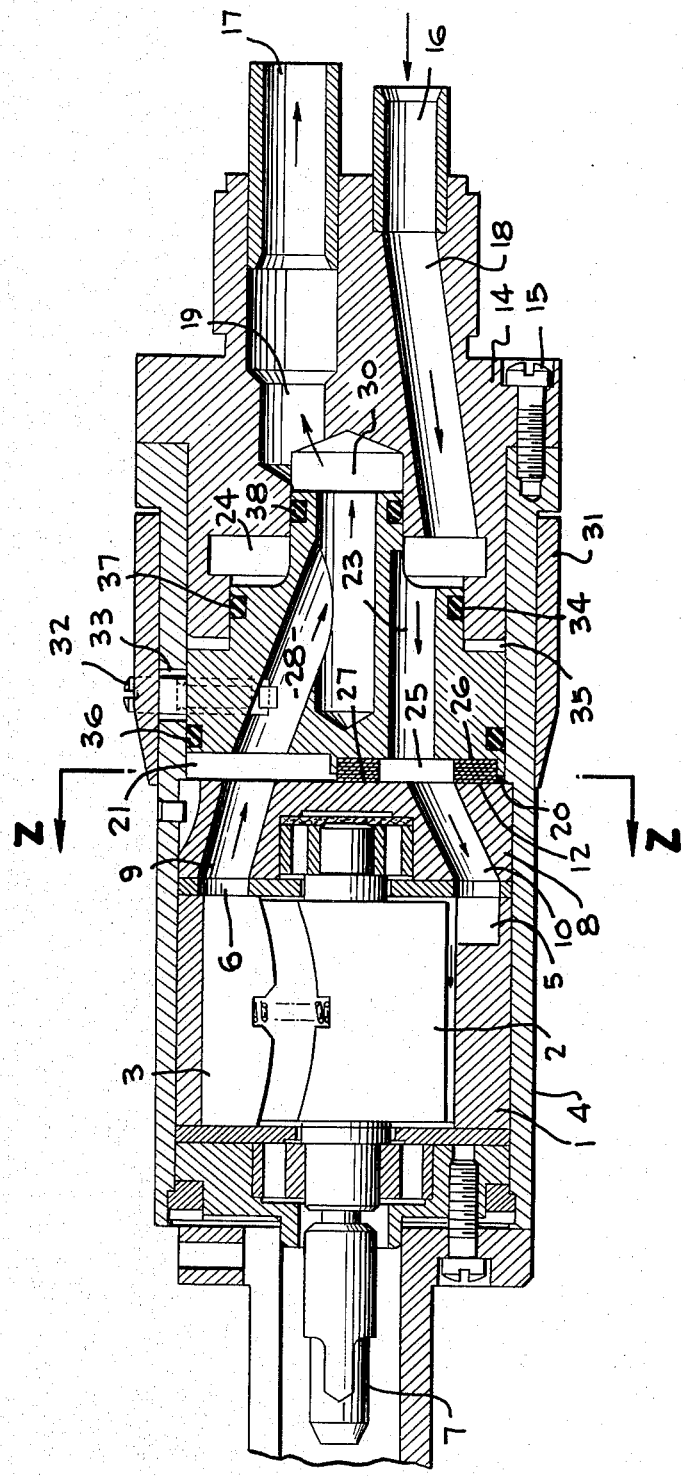
FIG. 1 is a partial longitudinal sectional view of an assembly comprising the motor block and the device for attaching it to a hand-held dental instrument, and the distribution block forming the subject of the invention.

As shown in FIG. 1, and in a manner known per se, the motor block is composed of a stator 1 and of a rotor 2 comprising vanes or blades 3, the assembly being arranged in a casing 4. The compressed air arrives through an orifice 5 and leaves through an outlet 6 causing rotation of the rotor and the shaft 7 to which it is connected, in a manner which is also known. The hand-held instrument to be driven is fixed on this shaft in a manner known per se (cf, for example, French Pat. No. 1,483,766 in the name of the Applicants).

A ring or end wall 8, which is made integral with the stator 1, is arranged at the downstream end of the motor block. This ring is traversed by first, second and third flow ducts 9, 10, and 11 respectively. The duct 9 is always an outlet. The ducts 10 and 11 are alternatively connected to a source of compressed air. Ducts 9, 10 and 11 merge inwardly at the end of wall 8 spaced from rotor 2 and are spaced at intervals of 120° about the axis of wall 8.

The duct 10 or alternatively 11 is supplied with compressed air by means of a distributor 13 forming the subject of the present invention. This distributor is also arranged inside the casing 4. It is held there by an internal casing 14 by means of fixing screws 15. The intake 16 of air originating from the compressed air source, the outlet 17 and optionally the water and air in the spray (not shown) are connected directly on this casing, through which corresponding ducts of the intake 18 and outlet 19 respectively are arranged.

The end 20 of the distributor 13 facing the wall 8 is shaped so as to define, on the one hand, an outflow chamber 21 having a crescent-shaped cross-section, this chamber communicating directly with the outlet orifice 9 of the ring and, on the other hand, a shoulder 22 of complementary shape.

The distributor 13 is traversed by a compressed air supply duct 23 in constant communication with the duct 18 whatever the position of the distributor 13 by means of an annular chamber 24 in which the two ducts 18 and 23 merge.

The duct 23 merges at the end 20 of the distributor through a circular opening 25 level with the shoulder 22, the said opening being surrounded by an annular seal end joint 26 of rectangular cross-section 27. The distributor 13 is also traversed by two outlet ducts 28, 29 merging, on the one hand, into the communication chamber 21 and uniting, on the other hand, in a single axial outlet duct 30 in constant communication with the duct 19.

The distributor 13 is made integral with an external sleeve 31 by means of a screw 32 capable of rotating in a corresponding groove 33 in the casing 4, the said screw acting as an abutment to limit this rotation to 120°.

Moreover, a surface 34 which is substantially perpendicular to the axis of the said distributor is arranged on the rear portion of the distributor. When the air arrives under pressure through the ducts 16 and 18, it fills the annular chamber 24 then traverses the duct 23 to arrive at the level of the ring 8. In this process, the air exerts a pressure on the surface 34 which causes the distributor 13 to urge the annular seal joint 26 against the face 12 of the wall 8 and thus to ensure the seal between the ducts 23 and the ducts 28 and 29. To compensate for this axial shifting of the distributor, an annular compensating chamber 35 will be provided, which is sufficiently wide to allow the clearance corresponding to the compression and the decompression of the seal joint 26 when the compressed air intake is cut off.

This chamber will communicate with the atmosphere to prevent a vacuum from forming in it. The surface 34 will be dimensioned so as to ensure a good seal while allowing easy rotation of the distributor. Finally, the O-rings needed, in addition to seal joint 26, to provide a perfect seal will be arranged round the distributor 13. The following are thus provided, respectively:

(a) the joint 36 providing the seal between the distributor 13 and the casing 4 in which it is arranged;

(b) the joint 37 providing the seal between the annular chamber 24 and the compensating chamber 35 which is open to the atmosphere;

(c) the joint 38 providing the seal between the annular chamber 24 and the outlet duct 30.

The arrangement of these joints ensures, on the one hand, a perfect seal between the inlet and the outlet, which allows use of the full power of the supplied air and, on the other hand, simple assembly which does not depend on the tolerances of usage or extent of stresses.

The distributor 13 which the operator rotates manually using the manoeuvrable sleeve 31 allows the distribution to be combined so as to have left-hand or right-hand running of the motor at a speed which can be controlled progressively from zero to its maximum in each of the rotational directions by progressive blocking of the inlet orifice 10 or 11 corresponding to the selected rotational direction, control being achieved by the annular end seal joint 26 whose rectangular cross-section 27 must be of a width in the operating position which is at least equal to the diameter of the delivery orifices of the ducts 10 and 11 on the face 12 which will be identical.

Figure 2:
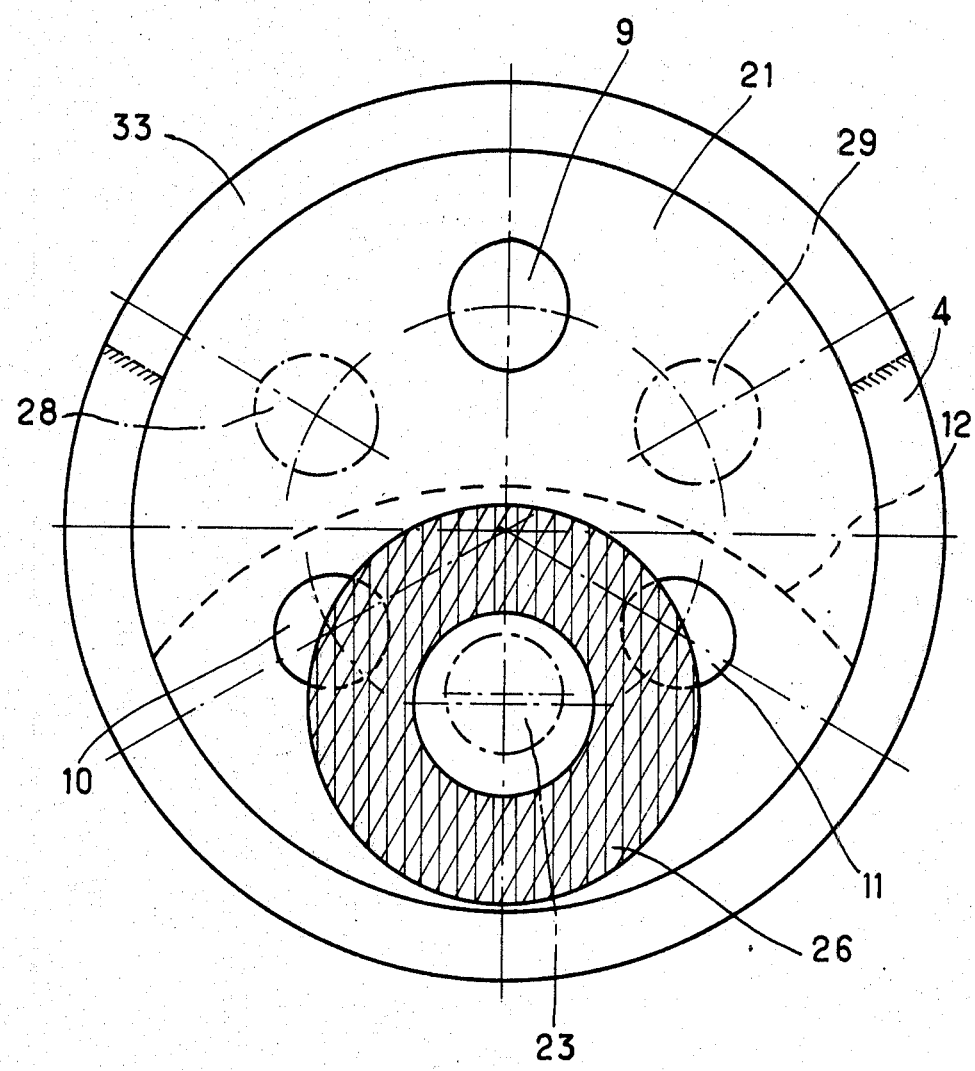
FIG. 2 shows a superimposed view of the relative positions of the ring orifices and the distributor orifices in the zero rotational speed position in a section along line ZZ.
Figure 3:
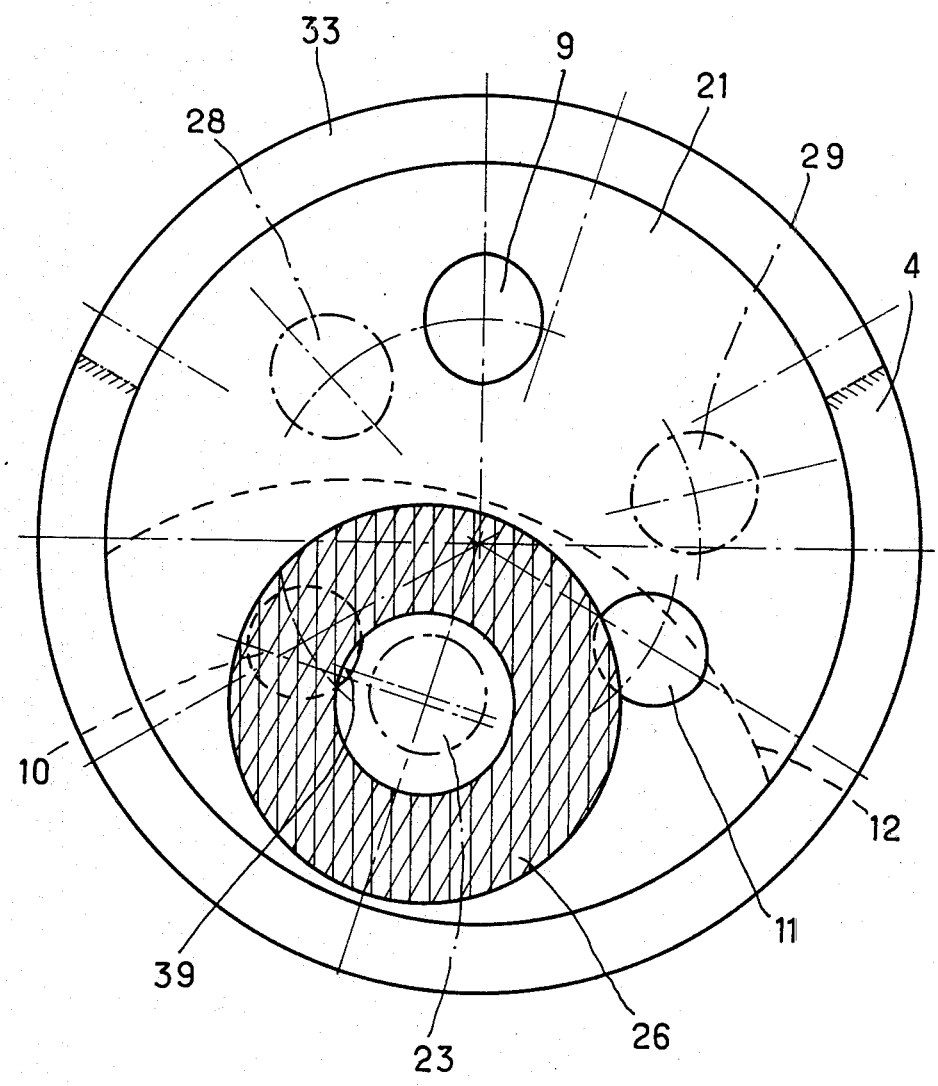
FIG. 3 shows a superimposed view of the relative positions of the ring orifices and the distributor orifices in the position for the start of rotation of the motor in a section along line ZZ.
Figure 4:
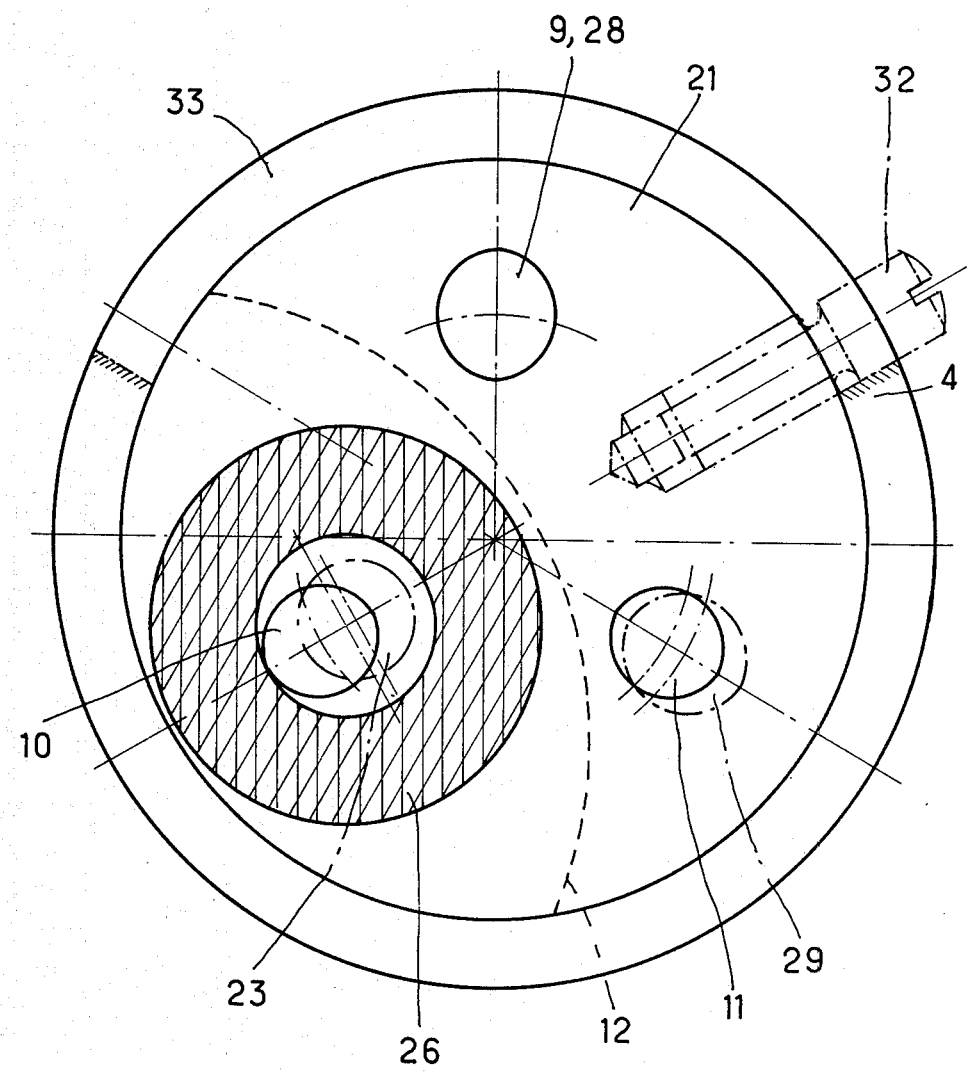
FIG. 4 shows in a superimposed view the relative positions of the ring orifices and the distributor orifices in the position of maximum speed of the motor in a section along line ZZ.

The functioning is explained in FIGS. 2, 3 and 4 which show the positions of ducts 9, 10, 11 on the one hand and 23, 28 and 29 respectively which are embodied by their delivery orifices on the face 12 of the ring 8 and on the face 20 of the distributor 13 respectively.

FIG. 2 shows the relative positions of the various ducts corresponding to the zero speed. The compressed air arriving through the duct 23 remains trapped against the wall of the ring 8 due to the action of the end annular seal joint 26. The orifices of the ducts 10 and 11 are partially covered by the seal joint 26 and, like the ducts 9, 28 and 29, communicate with the chamber 21 of the crescent-shaped cross-section, which is limited on the one hand by the shoulder 22 and on the other hand by the casing 4 in which the port 33 is arranged at 120°.

FIG. 3 shows the relative positions of the ducts of the distributor and of the ring when the sleeve 31 is turned manually. To reach this position, the seal joint 26 completely blocks the orifice of the duct to be supplied, 10 in this case, in the first stage. This is achieved due to the fact that the length of the rectangular cross-section of the said joint is at least equal to the diameter of the orifices of the ducts 10 and 11 in the operating condition. This is essential to the proper working of the distributor. In fact, when the duct 23 first communicates with the duct 10 as shown in FIG. 3 to determine a passage indicated by 39, the other portion of the orifice of the duct 10 is still blocked, otherwise the duct 23 would communicate with the chamber 21, that is to say the supply and the outlet would communicate upstream of the motor.

Of course, the device could still operate in this way, but the rotational speed would not progress regularly from zero to its maximum speed and would pass directly to a speed having a certain value below which the intermediate speeds between zero and this value could not be achieved.

In this position, the orifice 11 is virtually completely liberated and operates as an outlet concomitantly with 9.

Finally, FIG. 4 shows the maximum running speed, the orifice 10 being completely freed by the seal joint 26. All the air arriving through 23 is thus directed toward the motor through the duct 10. In this external position, the screw 32 acts as an abutment at the bottom of the port 33.

To reverse the rotational direction, the same operations would be performed by rotating the sleeve 31 in the opposite direction and by supplying the duct 11.

I claim:

1. A motor control system comprising:
   a casing;
   a blade-type motor including a rotor chamber in which a rotor is positioned; said motor being mounted in said casing;
   a rotary air distributor positioned inside said casing for both rotation about and movement along its axis;
   said distributor being freely slidably movable along its axis to at least a limited extent;
   a manually operated actuator positioned externally of said casing and connected to said distributor for permitting the manual rotation of said distributor;
   one end of said rotor chamber being defined by an end wall having first, second, and third flow ducts extending through said end wall and positioned with a spacing of 120° between adjacent ones of said flow ducts;
   said first flow duct always comprising an outlet opening for discharging exhausted drive air with said second and third flow ducts being of the same size and shape and being alternatively employed as either an inlet opening or an outlet opening in accordance with the rotational direction selected for the motor;
   wherein said distributor includes an inner end facing said end wall and which inner end includes an outflow chamber which is in communication with said first flow duct for all rotary positions of adjustment of said distributor;
   outlet duct means in said distributor communicating said outflow chamber with the atmosphere;
   said distributor additionally including a compressed-air supply duct having an inner end in facing relationship to said end wall and having an outer end connected to a source of compressed air;
   a seal joint fixedly mounted on the inner end of the distributor and including a central opening surrounding said inner end of the compressed-air intake duct and having an outer surface facing said end wall to provide a sealed connection of said air supply duct with said one end wall for all positions of adjustment of the distributor;
   means for urging said distributor axially toward said end wall; and
   wherein said distributor is capable of rotation from a first position in which the inner end of said compressed-air supply duct is aligned with said second flow duct and said first and third flow ducts communicate with said outflow chamber so as to effect rotation of the motor in a first direction through an intermediate position in which said inner end of said compressed-air supply duct is blocked by said end wall so that the motor does not rotate to a second position in which the inner end of said compressed-air supply duct is aligned with said third flow duct and said first and second flow ducts communicate with said outflow chamber so as to effect rotation of said motor in a second direction opposite to said first direction.

2. A motor control system as recited in claim 1 wherein said manually operated actuator is a sleeve connected to the distributor.

3. A motor control system as recited in claim 1 wherein said seal joint extends outward radially from its central opening an amount greater than the diameter of said second and third flow ducts so as to be capable of completely blocking one or the other of said second or third flow ducts as the distributor moves between either its first or second position and its intermediate position.

4. A motor control system as recited in either of claims 1 or 3 wherein said means for urging said distributor comprises an air chamber containing compressed air acting on a surface of said distributor.

5. A motor control system as recited in claim 1 wherein said outflow chamber in said distributor is a cresent-shaped chamber;

said cresent-shaped chamber communicating with said first flow duct and said second flow duct when said distributor is in its first position and communicating with said first flow duct and said third flow duct when said distributor is in its second position but communicating solely with said first flow duct when said distributor is in its intermediate position.

6. A motor control system as recited in claim 5 wherein said seal joint extends outward radially from its central opening an amount greater than the diameter of said second and third flow ducts so as to be capable of completely blocking one or the other of said second or third flow ducts as the distributor moves between either its first or second position and its intermediate position.

7. A motor control system as recited in claim 5 wherein said means for urging said distributor comprises a compressed-air chamber in said casing communicating with a surface of said distributor.

8. A motor control system as recited in claim 7 wherein said seal joint extends outward radially from its central opening an amount greater than the diameter of said second and third flow ducts so as to be capable of completely blocking one or the other of said second or third flow ducts as the distributor moves between either its first or second position and its intermediate position.

* * * * *